United States Patent [19]
Tsujino et al.

[11] Patent Number: 5,833,969
[45] Date of Patent: Nov. 10, 1998

[54] AQUEOUS COSMETIC COMPOSITION CONTAINING STABLY SOLUBILIZED URIC ACID AND AMPHOTERIC SURFACTANT AND METHOD FOR STABLY SOLUBILIZING URIC ACID IN AQUEOUS COSMETIC COMPOSITION

[75] Inventors: Yoshio Tsujino; Akiko Ogata; Kazuyo Tomura, all of Osaka, Japan

[73] Assignee: Yamahatsu Sangyo Kaisha, Ltd., Osaka-fu, Japan

[21] Appl. No.: 903,414

[22] Filed: Jul. 30, 1997

[30]  Foreign Application Priority Data

Jun. 25, 1997  [JP]  Japan .................................. 9-168495

[51] Int. Cl.$^6$ ................................ A61K 7/06; A61K 9/00
[52] U.S. Cl. .................................... 424/70.122; 424/70.1; 424/70.21; 424/401; 424/690; 424/691; 424/692; 424/693; 424/719; 424/722
[58] Field of Search ........................... 424/70.1, 70.122, 424/70.2, 401, 690, 691, 692, 693, 719, 722

[56]  References Cited

U.S. PATENT DOCUMENTS 4,961,925  10/1990  Tsujino et al. ............................ 424/71

FOREIGN PATENT DOCUMENTS

| 0716846A1 | 6/1996 | European Pat. Off. . |
|---|---|---|
| 61-118312 | 6/1986 | Japan . |
| 61-183204A | 8/1986 | Japan . |
| 1-275511A | 11/1989 | Japan . |
| 1-275516A | 11/1989 | Japan . |

*Primary Examiner*—James O. Wilson
*Attorney, Agent, or Firm*—Birch, Stewart, Kolasch & Birch, LLP

[57]  ABSTRACT

An aqueous cosmetic composition containing uric acid in a stably solubilized state together with 0.01 to 1.3% by weight of one or more amphoteric surfactants selected from the group consisting of (a) lauric acid amide propyl betaine, (b) alkyl carboxymethyl hydroxyethyl imidazolinium betaine, (c) coconut oil fatty acid amide propylmethylaminoacetic acid betaine, (d) sodium salt of coconut oil fatty acid acyl carboxymethyl hydroxyethyl ethylenediamine, (e) lauryl dimethylaminoacetic acid betaine and (f) coconut oil alkyl betaine, an alkali and water. The composition is adjusted to pH equal to or higher than $pK_1$ of uric acid with the alkali to solubilize uric acid. A method for stably solubilizing uric acid in an aqueous cosmetic composition is also disclosed.

8 Claims, 2 Drawing Sheets

AQUEOUS COSMETIC COMPOSITION CONTAINING STABLY SOLUBILIZED URIC ACID AND AMPHOTERIC SURFACTANT AND METHOD FOR STABLY SOLUBILIZING URIC ACID IN AQUEOUS COSMETIC COMPOSITION

FIELD OF THE INVENTION

The present invention relates to an aqueous cosmetic composition containing stably solubilized uric acid, a specific amphoteric surfactant, an alkali and water, and a method for stably solubilizing uric acid in an aqueous cosmetic composition.

BACKGROUND OF THE INVENTION

Uric acid as well as its salt and derivative (hereinafter they are simply referred to as "uric acid" altogether) are used in various cosmetic compositions as a substrate of one of oxidases, uricase, a stabilizer of a moisturizer, an ingredient for preventing skin roughness, an antidandruff ingredient and the like. For example, JP 61-118312 A discloses a keratin fiber dyeing composition of pH 4 to 10.5 which comprises uric acid, an amphoteric surfactant, a thickener and the like and a method for dyeing keratin fiber using the composition. JP 61-183204 A discloses a cosmetic composition comprising a moisturizer and uric acid as a stabilizer for the moisturizer. JP 63-246313 A (U.S. Pat. No. 4,961,925) discloses a hair cosmetic composition of pH 7.5 to 8.5 which comprises dielectron reducing oxidase, uric acid as a donor of the enzyme and the like. JP 1-275511 A discloses a topical composition for skin external use containing uric acid for preventing skin roughness. JP 1-275516 A discloses an antidandruff composition containing uric acid. JP 8-217652 (EP 0716846 A) discloses an oxidation hair dyeing composition of pH 6.7 to 9.5 which comprises uric acid, potassium hydroxide and/or monoethanolamine and the like.

On the other hand, since the water-solubility of uric acid is very low such as about 0.0067%, at present, only a small amount of uric acid can be used in case of an aqueous solubilized system. In addition, in case of a dispersion system wherein uric acid is added in excess of its solubility, there are many problems such as precipitation of uric acid, limitation of containers to be used for packaging end products due to clogging of orifices thereof and the like.

Moreover, although uric acid can be solubilized in water to a certain extent by appropriately choosing an alkali, mere solubilization is insufficient for practical use due to such problems as drip and less fitness for hair or skin upon application, and the like. Then, in practice, it is necessary to add surfactants and polymers in view of usability.

However, in aqueous cosmetic compositions containing surfactants and polymers, no satisfactory technique for stably solubilizing uric acid has yet been found.

OBJECTS OF THE INVENTION

One object of the present invention is to provide a technique for stably solubilizing uric acid in an aqueous cosmetic composition containing uric acid and a specific amount of a specific amphoteric surfactant.

This object as well as other objects and advantages of the present invention will become apparent to those skilled in the art from the following description with making reference to the accompanying drawings.

SUMMARY OF THE INVENTION

Figure 1:
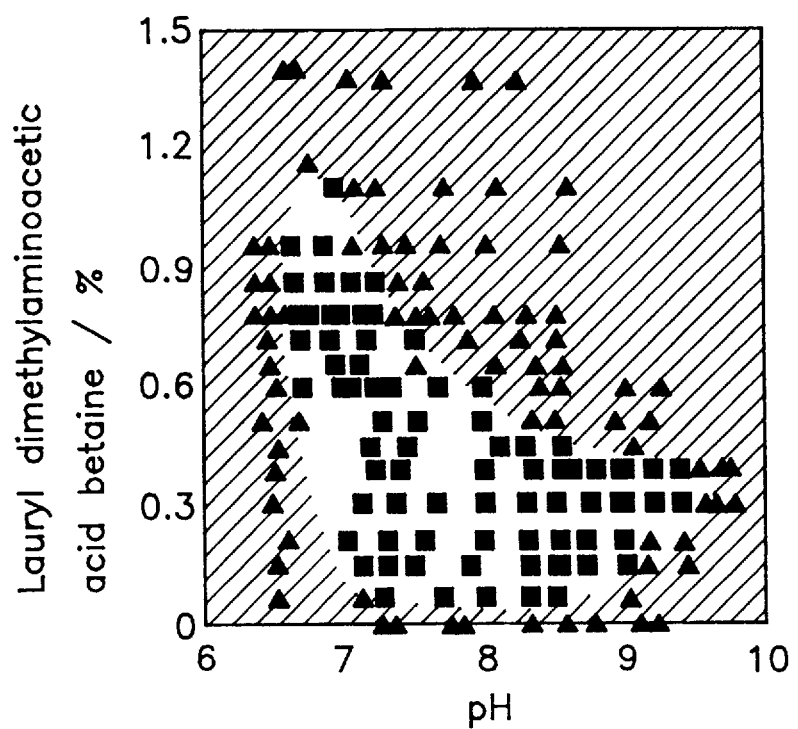
FIG. 1 illustrates influence of the amount of an amphoteric surfactant and pH of a composition on 0.5% solubilized uric acid.

The present inventors have intensively studied behavior of uric acid in an aqueous cosmetic composition. As a result, it has been found that uric acid can be stably solubilized in such a composition by combining a specific amphoteric surfactant and an alkali and adjust pH of the composition to a specific range.

That is, in one aspect, the present invention provides an aqueous cosmetic composition containing uric acid in a stably solubilized state which comprises uric acid, 0.01 to 1.3% by weight of one or more amphoteric surfactants selected from the group consisting of (a) lauric acid amide propyl betaine, (b) alkyl carboxymethyl hydroxyethyl imidazolinium betaine, (c) coconut oil fatty acid amide propylmethylaminoacetic acid betaine, (d) sodium salt of coconut oil fatty acid acyl carboxymethyl hydroxyethyl ethylenediamine, (e) lauryl dimethylaminoacetic acid betaine and (f) coconut oil alkyl betaine, an alkali, and water;

said composition being adjusted to pH equal to or higher than $pK_1$ of uric acid, in particular, pH 6.5 to 9.5 by the alkali to solubilize uric acid.

In another aspect, the present invention provides a method for stably solubilizing uric acid in an aqueous cosmetic composition together with the above amphoteric surfactant which comprises adjusting pH of the composition equal to or higher than $pK_1$ of uric acid, in particular, pH 6.5 to 9.5 by an alkali to solubilize uric acid.

According to the present invention, a relatively large amount of uric acid such as 0.01 to 2.5% by weight can be stably solubilized to provide an aqueous cosmetic composition, for example, hair dyeing composition which exhibits excellent activity of uric acid and sufficient effect of the amphoteric surfactant.

DETAILED DESCRIPTION OF THE INVENTION

The terms "stably solubilizing" and "stably solubilized state" used herein mean that uric acid is maintained in a solubilized state without separation in a cosmetic composition.

Examples of uric acid to be used in the present invention includes, in addition to uric acid itself, inorganic salts of uric acid such as sodium urate, potassium urate, calcium urate, sodium hydrogen urate, potassium hydrogen urate, calcium hydrogen urate, etc.; organic salts of uric acid such as ammonium urate, ammonium hydrogen urate, salts of uric acid with various amino acids, etc.; and various uric acid derivatives such as alkyl modified uric acids (e.g., 3-N-methyl uric acid, 3-N-lauryl uric acid, 7-N-butyl uric acid, 1-N-ethyl uric acid, 9-N-lauryl uric acid, 3,7-N-dimethyl uric acid, etc.), uric acid glycosides (e.g., 3-N-ribosyl uric acid, 9-N-glycosyl uric acid, etc.) and the like.

These uric acid, salts and derivatives can be used alone or in combination and can be used in an amount of, as uric acid itself, 0.01 to 2.5% by weight based on the total weight of the cosmetic composition. When the amount of uric acid is lower than 0.01% by weight, its activity is insufficient. On the other hand, when the amount of uric acid is more than 2.5% by weight, stable solubilization thereof is hardly expected.

The amphoteric surfactant to be used in the present invention is (a) lauric acid amide propyl betaine, (b) $C_{11\text{-}17}$ alkyl carboxymethyl hydroxyethyl imidazolinium betaine, (c) coconut oil fatty acid amide propylmethylaminoacetic acid betaine, (d) sodium salt of coconut oil fatty acid acyl ($C_{8\text{-}18}$) carboxymethyl hydroxyethyl ethylenediamine, (e) lauryl dimethylaminoacetic acid betaine and (f) coconut oil alkyl ($C_8$-18) betaine. The amphoteric surfactant can be used alone or in combination thereof. The amount of the amphoteric surfactant(s) is 0.01 to 1.3% by weight based on the total weight of the composition. When the amount is lower than 0.01% by weight or more than 1.3% by weight, the desired solubilization of uric acid is hardly expected.

Examples of the alkali to be used in the present invention include amines such as monoethanolamine (MEA), diethanolamine (DEA), triethanolamine (TEA), 2-amino-2-methyl-1-propanol (AMP), 2-amino-2-methyl-1,3-propanediol (AMPD), monoisopropanolamine (MIPA), tetrakis(2-hydroxyisopropyl) ethylenediamine (TE) and the like. These alkalis can be used alone or in combination and it is possible to use ammonia and inorganic alkalis such as sodium hydroxide, potassium hydroxide and the like. Although the amount of the alkali to be added to the composition is not specifically limited, the amount should be sufficient for adjusting pH of the composition equal to or higher than $pK_1$ of uric acid, preferably, pH 6.5 to 9.5. Thereby, uric acid can be stably solubilized in an aqueous cosmetic composition.

Especially, in the present invention, it is preferred to use an amine as the alkali together with the amphoteric surfactant because uric acid can be solubilized very stably.

According to the present invention, uric acid is added to a major portion of water to be used for the production of the aqueous cosmetic composition and pH of the resultant mixture is adjusted to the desired pH, followed by addition of the amphoteric surfactant and, if necessary, warming to dissolve the polymer. Then, other ingredients are added to obtain the desired aqueous cosmetic composition in various preparation forms such as gel, paste, cream and the like. Thus, an aqueous cosmetic composition for application to hair, skin, nails, oral cavity or the like, which contains stably solubilized uric acid together with the acrylic polymer can be obtained.

In the present invention, according to the desired preparation form, surfactants such as nonionic surfactants, etc.; oily agents such as higher alcohols, higher fatty acids, paraffin wax, hydrocarbon oils, ester oils, silicone oils, etc.; hair dyes such as oxidation dyes, direct dyes, etc.; moisturizers such as glycerin, propylene glycol, etc.; thickeners; preservatives; anti-oxidants; UV absorbers; metal chelating agents; enzymes such as uricase; various pharmacologically active ingredients; perfumes; and the like can be appropriately added in so far as they do not adversely affect the present invention.

The following tests and examples further illustrate the present invention in detail but are not to be construed to limit the scope of the present invention. In the tests and examples, all the "percents (%)" are by weight unless otherwise stated.

Test 1

Influence of various surfactants on solubilization of uric acid

According to the following formulation, a solution was prepared by using an amine, 2-amino-2-methyl-1,3-propanediol (AMPD) as a pH adjusting agent. After storing the solution at 5° C. for 3 days, the state of uric acid was observed by the naked eye.

Formulation of solution

| Ingredient | Amount (%) |
| --- | --- |
| Uric acid | 0.5 |
| AMPD | pH 6.5–10.0 balance |
| Surfactant to be tested | 0.15 |
| $KH_2PO_4$ | 0.2 |

Surfactants tested were as follows.
Anionic surfactant: triethanol amine lauryl sulfate (A);
Cationic surfactant: stearyl trimethylammonium chloride (B); and
Amphoteric surfactants: lauric acid amide propyl betaine (C), 2-$C_{11\text{-}17}$ alkyl-N-carboxymethyl-N-hydroxyethyl imidazolinium betaine (D), sodium salt of N-coconut oil fatty acid acyl-N-carboxymethyl-N-hydroxyethyl ethylenediamine (E), N-coconut oil fatty acid amide propylmethylaminoacetic acid betaine (F), lauryl dimethylaminoacetic acid betaine (G) and coconut oil alkyl betaine (H).

The results are shown in Table 1.

TABLE 1

| | pH | | | | | | | |
| --- | --- | --- | --- | --- | --- | --- | --- | --- |
| Surfactant | 6.5 | 7.0 | 7.5 | 8.0 | 8.5 | 9.0 | 9.5 | 10.0 |
| Blank | P | P | P | P | P | P | P | P |
| A | P | P | P | P | P | P | P | P |
| B | P | P | P | P | P | P | P | P |
| C | P | P | P | S | P | P | P | P |
| D | P | P | S | P | P | P | P | P |
| E | P | P | S | S | P | P | P | P |
| F | P | P | S | S | P | P | P | P |
| G | P | P | S | S | S | P | P | P |
| H | P | P | S | S | S | P | P | P |

S: uric acid solubilized
P: uric acid precipitated

As can be seen from Table 1, it has been shown that the anionic and cationic surfactants influence on sulbilization of uric acid negatively. In addition, the amphoteric surfactants solubilize uric acid in a certain specific range.

Test 2

Influence of various alkalis on solubilization of uric acid

According to the following formulation, a solution was prepared by using lauryl dimethylaminoacetic acid betaine which showed the broadest uric acid-solubilization range in the above Test 1. After storing the solution at 5° C. for 3 days, the state of uric acid was observed by the naked eye.

Formulation of solution

| Ingredient | Amount (%) |
| --- | --- |
| Uric acid | 0.5 |
| Alkali to be tested | pH 6.5–10.0 balance |
| Lauryl dimethylaminoacetic acid betaine | 0.15 |
| $KH_2PO_4$ | 0.2 |

Alkalis tested were as follows.
Inorganic alkalis: sodium hydroxide and potassium hydroxide; and
Amines: monoethanolamine (MEA), diethanolamine (DEA), triethanolamine (TEA), 2-amino-2-methyl-1- propanol (AMP), 2-amino-2-methyl-1,3-propanediol (AMPD), 2-amino-2hydroxymethyl-1,3-propanediol (AHMPD) and monoisopropanolamine (MIPA).

The results are shown in Table 2.

TABLE 2

| Alkali | pH | | | | |
|---|---|---|---|---|---|
| | 6.5 | 7.0 | 8.0 | 9.0 | 9.5 |
| NaOH | P | P | P | P | P |
| KOH | P | P | P | P | P |
| AMP | P | P | S | S | P |
| MIPA | P | P | S | S | S |
| DEA | P | P | S | S | S |
| MEA | P | P | S | S | S |
| TEA | P | P | S | — | — |
| AHMPD | P | P | S | — | — |
| AMPD | P | S | S | S | P |

S: uric acid solubilized
P: uric acid precipitated
—: pH unadjustable

As can be seen from Table 2, it has been shown that the inorganic alkalis influence on solubilization of uric acid negatively, while the amines influence on solubilization positively.

Test 3

Influence of amount of amphoteric surfactant and pH of composition on solubilization of uric acid According to the following formulation, a solution was prepared by using lauryl dimethylaminoacetic acid betaine as the amphoteric surfactant and AMPD as the alkali. After storing the solution at 5° C. for 3 days, the state of uric acid was observed by the naked eye.

| Formulation of solution | |
|---|---|
| Ingredient | Amount (%) |
| Uric acid | 0.5 or 1.0 |
| AMPD | pH 6.5–10.0 balance |
| Lauryl dimethylaminoacetic acid betaine | 0–1.5 |
| KH$_2$PO$_4$ | 0.2 |

Figure 2:
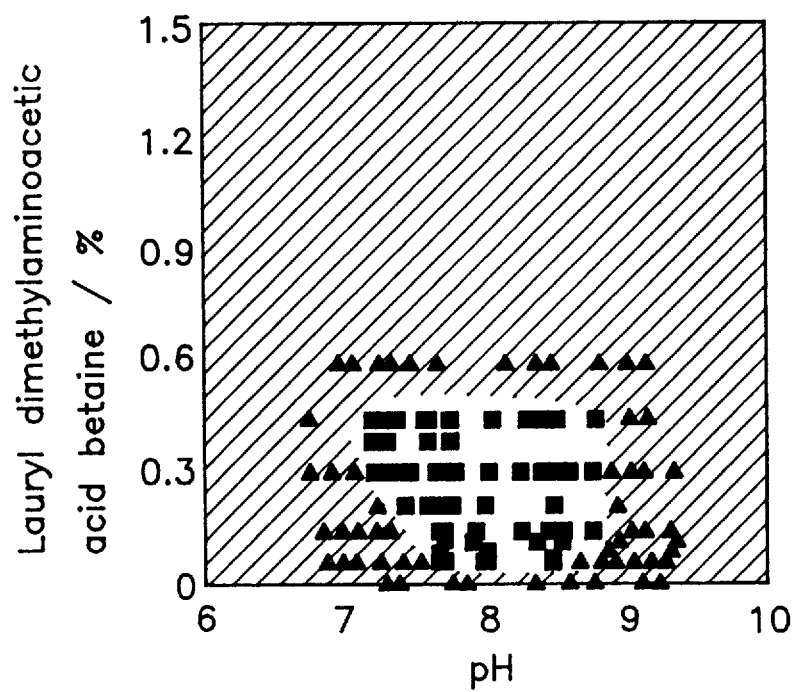
FIG. 2 illustrates influence of the amount of an amphoteric surfactant and pH of a composition on 1.0% solubilized uric acid.

The results are shown in FIGS. 1 and 2. In FIGS. 1 and 2, the vertical axis represents concentration of lauryl dimethylaminoacetic acid betaine (%) and the horizontal axis represents pH. The closed square represents solubilization of uric acid and the closed triangle represents precipitation of uric acid. The shaded part represents uric acid-precipitation range and the open part represents uric acid-solubilization range.

As can be seen from FIGS. 1 and 2, solubilization of uric acid depends on both amount of the amphoteric surfactant and pH of the composition. It has been found that, as concentration of uric acid increases, uric acid-solubilization range becomes smaller.

Test 4

Examination of uric acid-solubilization range

According to the following formulation, a solution was prepared by using lauryl dimethylaminoacetic acid betaine as the amphoteric surfactant and AMPD as the alkali. After storing the solution at 5° C. for 3 days, the state of uric acid was observed by the naked eye.

| Formulation of solution | |
|---|---|
| Ingredient | Amount (%) |
| Uric acid | 0.5 to 3.0 |
| AMPD | pH 8.0–9.0 balance |
| Lauryl dimethylaminoacetic acid betaine | 0.3 |
| KH$_2$PO$_4$ | 0.2 |

The results are shown in Table 3

TABLE 3

| pH | Uric acid (%) | | | | | |
|---|---|---|---|---|---|---|
| | 0.5 | 1.0 | 1.5 | 2.0 | 2.5 | 3.0 |
| 8.0 | S | S | P | P | P | P |
| 8.5 | S | S | S | S | P | P |
| 9.0 | S | S | S | S | S | P |

S: uric acid solubilized
P: uric acid precipitated

As can be seen from Table 3, it has been shown that up to 2.5% by weight of uric acid is solubilized in a system using both amphoteric surfactant and alkali.

EXAMPLE 1

One-package hair dye (gel)

| Ingredient | Amount (%) |
|---|---|
| Uric acid | 1.0 |
| AMPD | pH 8.3 balance |
| Lauryl dimethylaminoacetic acid betaine | 1.0 |
| p-Phenylenediamine | 1.5 |
| m-Phenylenediamine hydrochloride | 0.08 |
| p-Aminophenol | 0.2 |
| m-Aminophenol | 0.04 |
| Cysteine | 0.17 |
| 1,3-Butylene glycol | 5.0 |
| Hydroxyethyl cellulose | 3.0 |
| Uricase (20 ku/g) | 1.0 |
| Purified water | balance |
| Total | 100.0 |

According to this formulation, uric acid was added to a part of water to be used and the mixture was adjusted to pH 8.3 with AMPD. Then, the remaining ingredients were added thereto to obtain the desired hair dye preparation.

This preparation was coated on a white hair, which was treated at 30° C. for 30 minutes, washed with water, shampooed and then dried. The white hair was dyed in grayish color.

EXAMPLE 2

Sunscreen milky lotion

| Ingredient | Amount (%) |
|---|---|
| Uric acid | 0.1 |
| AMPD and KH$_2$PO$_4$ | pH 7.0 balance |
| Coconut oil alkyl betaine | 0.3 |
| Polyoxyethylene(5) alkyl ether | 1.0 |
| Decaglycerol monoleate | 0.5 |
| Cetanol | 0.2 |

-continued

| Ingredient | Amount (%) |
| --- | --- |
| Purified water | balance |
| Total | 100.0 |

Uric acid was added to water and dissolved with AMPD. The remaining ingredients were added to the mixture and the resultant mixture was adjusted to pH 7.0 to obtain the desired sunscreen milky lotion.

EXAMPLE 3

Hand cream

| Ingredient | Amount (%) |
| --- | --- |
| Uric acid | 0.2 |
| AMPD and $KH_2PO_4$ | pH 7.0 balance |
| Lauryl dimethylaminoacetic acid betaine | 0.3 |
| Stearic acid | 14.0 |
| Vaseline | 1.5 |
| Self-emulsifiable glycerol monostearate | 2.5 |
| Polyoxyethylene(20)sorbitan monostearate | 1.5 |
| Propylene glycol | 0.174 |
| Perfume | 0.05 |
| Methylparaben | 0.05 |
| Purified water | balance |
| Total | 100.0 |

Uric acid was added to water and dissolved with AMPD. The remaining ingredients were added to the mixture and the resultant mixture was adjusted to pH 7.0 to obtain the desired hand cream.

EXAMPLE 4 one-package hair dye (cream)

| Ingredient | Amount (%) |
| --- | --- |
| Uric acid | 1.0 |
| AMPD | pH 8.3 balance |
| Coconut oil alkyl betaine | 1.0 |
| p-Phenylenediamine | 1.5 |
| p-Phenylenediamine hydrochloride | 0.08 |
| p-Aminophenol | 0.2 |
| m-Aminophenol | 0.04 |
| Cysteine | 0.17 |
| Polyoxyethylene(10) cetyl ether | 8.0 |
| Stearyl alcohol | 2.5 |
| Oleyl alcohol | 5.0 |
| Behenyl alcohol | 2.0 |
| Cetyl alcohol | 2.0 |
| Tetrakis(2-hydroxyisopropyl)ethylenediamine | pH 8.5 balance |
| Uricase (20 ku/g) | 1.0 |
| Purified water | balance |
| Total | 100.0 |

The ingredients except uricase, a part of water and AMPD were mixed with heating. After cooling, the remaining water and uricase were added thereto and the mixture was adjusted to pH 8.3 with AMPD to obtain the desired hair dye preparation.

This preparation was coated on a white hair, which was treated at 30° C. for 30 minutes, washed with water, shampooed and then dried. The white hair was dyed in brownish color.

As described hereinabove, according to the present invention, an aqueous cosmetic composition containing stably solubilized uric acid which can exhibit sufficient effect of uric acid can be obtained.

What is claimed is:

1. An aqueous cosmetic composition containing uric acid in a stably solubilized state which comprises uric acid, 0.01 to 1.3% by weight of one or more amphoteric surfactants selected from the group consisting of (a) lauric acid amide propyl betaine, (b) alkyl carboxymethyl hydroxyethyl imidazolinium betaine, (c) coconut oil fatty acid amide propylmethylaminoacetic acid betaine, (d) sodium salt of coconut oil fatty acid acyl carboxymethyl hydroxyethyl ethylenediamine, (e) lauryl dimethylaminoacetic acid betaine and (f) coconut oil alkyl betaine, an alkali and water, and said composition being adjusted to pH equal to or higher than $pK_1$ of uric acid with the alkali to solubilize uric acid.

2. A composition according to claim 1, wherein the composition is adjusted to pH 6.5 to 9.5.

3. A composition according to claim 1, wherein the composition contains 0.01 to 2.5% by weight of uric acid.

4. A composition according to claim 1, wherein the alkali is an amine.

5. A method for stably solubilizing uric acid in an aqueous cosmetic composition comprising uric acid, 0.01 to 1.3% by weight of one or more amphoteric surfactants selected from the group consisting of (a) lauric acid amide propyl betaine, (b) alkyl carboxymethyl hydroxyethyl imidazolinium betaine, (c) coconut oil fatty acid amide propylmethylaminoacetic acid betaine, (d) sodium salt of coconut oil fatty acid acyl carboxymethyl hydroxyethyl ethylenediamine, (e) lauryl dimethylaminoacetic acid betaine and (f) coconut oil alkyl betaine, an alkali and water, said method comprising adjusting pH of the composition equal to or higher than $pK_1$ of uric acid with an alkali to solubilize uric acid.

6. A method according to claim 5, wherein the composition is adjusted to pH 6.5 to 9.5.

7. A method according to claim 5, wherein the composition containing 0.01 to 2.5% by weight of uric acid.

8. A method according to claim 5, wherein the alkali is an amine.

* * * * *